United States Patent [19]

Lerner

[11] Patent Number: 4,608,869
[45] Date of Patent: Sep. 2, 1986

[54] SINGLE PARTICLE DETECTION SYSTEM

[75] Inventor: Cathy M. Lerner, Rehovot, Israel

[73] Assignee: Trustees of Boston University, Boston, Mass.

[21] Appl. No.: 622,642

[22] Filed: Jun. 20, 1984

Related U.S. Application Data

[63] Continuation-in-part of Ser. No. 409,929, Aug. 20, 1982, abandoned.

[51] Int. Cl.[4] ............................................. G01N 29/00
[52] U.S. Cl. ........................................ 73/644; 73/32 A
[58] Field of Search ................. 73/19, 32 A, 634, 642, 73/644, 646, 647, 602, 432 PS; 310/334, 335, 336; 367/7, 13, 150

[56] References Cited

U.S. PATENT DOCUMENTS

| | | | |
|---|---|---|---|
| 2,762,447 | 9/1956 | Cady | 73/646 |
| 2,912,853 | 11/1959 | Hanysz | 73/642 |
| 2,992,553 | 7/1961 | Joy | 73/636 |
| 3,508,436 | 4/1970 | Krautkramer | 73/644 |
| 3,913,386 | 10/1975 | Saglio | 73/642 |
| 4,063,549 | 12/1977 | Beretsky et al. | 73/602 |
| 4,381,674 | 5/1983 | Abts | 73/599 |
| 4,407,838 | 10/1983 | Schomberg | 73/602 |

OTHER PUBLICATIONS

Moyer, Expanding the Capability of a Laboratory Testing Facility, Oct. 1973, pp. 193–204, Materials Evaluation.
Finger, Measurements of Low-Velocity Flow Noise on Pressure and Pressure Gradient Hydrophones, Jun. 79, pp. 1407–1411, Journal Acoust. Soc. Am. 65(6).
Sinclair, High Resolution Acoustic Probe, Oct. 1980, pp. 805–806, Electronics Letters, vol. 16, No. 21.
R. V. Murphy, Toroidal, Conical and Spherical Lenses in Ultrasonic Inspection, *Materials Evaluation*, 39 (Mar. 1981), pp. 391–395.
Rubens A. Sigelmann and John M. Reid, Analysis and Measurement of Ultrasound Backscatting from an Ensemble of Scatters Excited by Sine-Wave Bursts, *The Journal of the Acoustical Society of America*, 53: 1351 (1973), No. 5, pp. 1351, 1354 and 1355.
T. Tarnoczy, Sound Focusing Lenses and Waveguides, *Ultrasonics*, (Jul.–Sep. 1965), pp. 115–127.
Victor C. Anderson, Sound Scattering from a Fluid Sphere, *The Journal of the Acoustical Society of America*, 22: No. 4 (Jul. 1950), pp. 426–431.
Richard K. Johnson, Sound Scattering from a Fluid Sphere Revisited, *The Journal of the Acoustical Society of America*, 61: No. 2, (Feb. 1977), pp. 375–377.
W. Kohn and J. R. Rice, Scattering of Long-Wavelength Elastic Waves from Localized Defects in Solids, *Journal of Applied Physics*, 50: No. 5, (May 1979), pp. 3346–3353.

*Primary Examiner*—Stewart J. Levy
*Assistant Examiner*—Robert R. Raevis
*Attorney, Agent, or Firm*—Hamilton, Brook, Smith & Reynolds

[57] ABSTRACT

In order to identify the density of a particle, an acoustic wave is focused on the particle and the reflected wave is detected by the focusing transducer. The ratio of the Fourier transform of the transmitted wave to the received wave is an indication of density. A particle to be examined may be suspended in a low boiling point medium and a transducer may be located within the medium by melting a localized region of medium by means of temperature control liquid flowing through the transducer assembly.

16 Claims, 6 Drawing Figures

SINGLE PARTICLE DETECTION SYSTEM

RELATED APPLICATIONS

This is a continuation-in-part of U.S. application Ser. No. 409,929, filed Aug. 20, 1982, now abandoned.

BACKGROUND

Acoustic systems have been used much like optic systems for imaging and analyzing subjects which are optically opaque. It has been suggested that many properties of a subject, such as its geometry, density distribution, and elastic properties of defects, can be analyzed from measurements of acoutic waves scattered from the subject. One problem of such systems is that the scattered acoustic waves include so much information that it is difficult to isolate a parameter of interest. It is further difficult to isolate a particular particle of interest from the surrounding environment.

DISCLOSURE OF THE INVENTION

In accordance with certain principles of this invention, an acoustic transducer lens is precisely located relative to a particle to be analyzed. The particle is suspended in a low boiling point medium such as gelatin. The particle may be suspended by providing a melted gel in a container, positioning the particle in the gel and then resolidifying the gel by circulating a cold temperature control liquid through the container walls. A focusing acoustic transducer is also positioned in the gel. A temperature control liquid can be circulated through the transducer housing to melt and then resolidify the gel immediately surrounding the transducer. The transducer can be moved through the locally melted gel and be positioned within microns of the particle without disturbing the position of the particle.

The transducer serves as a combined focusing acoustic transmitter and focused acoustic receiver. It has been determined that the ratio of the Fourier transform of the transmitted wave to that of the received wave is indicative of the density of a particle at the focal point of the transducer. By positioning the lens and particle in a gel, the characteristic reflections from different density particles can be identified. By using those reflections as a reference, one can then observe particles in some other medium, such as biological tissue, to characterize those particles.

The temperature control gel container also allows for embedding other acoustic devices such as a hydrophone. By moving the hydrophone in the gel relative to a lens, for example, characteristics of the lens can be identified.

In a preferred embodiment, the transducer comprises a front section into which the lens is formed and through which a liquid conduit extends adjacent to the lens, a back section having a liquid chamber therein and a piezoelectric element sandwiched between the two sections.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DESCRIPTION OF PREFERRED EMBODIMENTS

Figure 1:
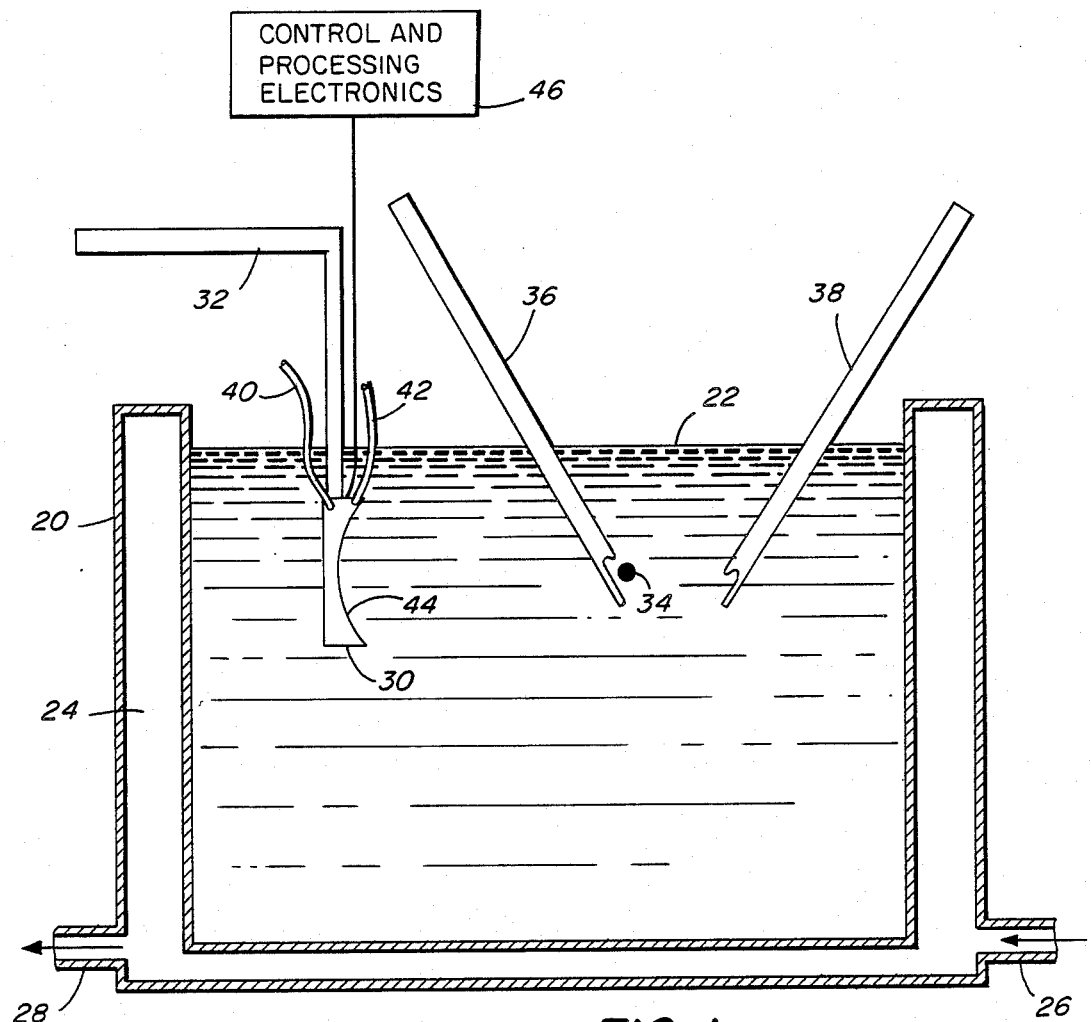
FIG. 1 illustrates positioning of a particle within a medium relative to an acoustic transducer in accordance with principles of the present invention.

As shown in FIG. 1, a container 20 is provided to hold an acoustic transmission medium 22 for acoustic tests. The chamber 20 has hollow walls and a hollow base to form a plenum 24. A plenum can be filled with temperature control liquid which is introduced through an inlet pipe 26 and drained through a drainpipe 28. By passing relatively high temperature liquid through the plenum, the temperature of the mass of gel 22 can be increased to a sufficient level to cause the gel to melt. Thereafter, the high temperature liquid can be drained from the plenum and colder liquid can be introduced to reduce the temperature of the gel 22 and cause it to solidify. The walls of the container 20 are preferably formed of plexiglass to minimize acoustic noise within the gel. It is preferably cylindrical with a radius of 6 to 10 centimeters. The plenum is about 2 centimeters wide in the walls of the container and 1 centimeter deep in the base.

An acoustic transducer 30 is suspended in the molten gel 22 by a brass holder 32. The holder may be mounted to an X-Y control device or an X-Y-Z control device. The particle 34 is placed in the gel with two 25 gauge needles 36 and 38 which are hand held. The particle is placed on the end of one needle 36 and both needles are placed in the soft, molten gel in front of the transducer 30. While the particle is being inserted with the needles into the gel, cold water is directed through the plenum so that the gel begins to harden. Then the particle is scraped off the needle 36 with the needle 38. As the particle is scraped from the needle 36, the gel is sufficiently solidified to suspend the particle, but it is still sufficiently soft to allow removal of the needles without leaving tracks in the gel or small bubbles around the particle. Such tracks or bubbles might result in spurious signals from reflected acoustic waves.

As will be described below, the transducer 30 has conduits therethrough for a temperature control liquid which can be passed through the transducer assembly from a tube 40 and to a tube 42. By initiating flow of warm water above 37.4° C. through the lens, the gel in the immediate area around the transducer melts. The temperature gradient is sufficiently localized, however, that gel spaced more than a few microns from the transducer 30 remains sufficiently solid to support the particle 34. When the transducer is in a position from which one would like to view the particle reflections, the warm water through the tranducer assembly is clamped off and cold water is continuously sent through the assembly to resolidify the area around the transducer.

Because the lens can be moved through the gel with respect to the particle, measurements of reflections can be made from all directions about the particle. Because the heating is localized, the transducer may be moved closer than one millimeter to the particle and even as close as one micron before the melting in front of the transducer causes the particle to move. In order to precisely locate the transducer relative to the particle, the entire system may be placed on a microscope table.

The gelatin mixture is made up of 4% gelatin and 0.9% saline solution. The gel has a melting point of 37.4° C. The transmission curves for the gel are the same as for water. The saline solution allows the use of electrolysis to produce small stationary bubbles in the gel. One may thus observe the reflections from single stationary air bubbles as well.

The transducer assembly 30 includes a piezoelectric crystal therein which transmits a pulsed, five to twelve megahertz acoustic wave through a lens face 44 of the assembly. The lens face 44 focuses the acoustic wave, and in a preferred use of the system, the acoustic wave is focused onto the particle 34; that is, the particle 34 is positioned in the focal plane of the lens. The particle reflects the incident acoustic wave to the crystal. The crystal then converts the reflected acoustic wave back into an electrical signal which can be applied to and observed on an oscilloscope. The reflected pulse may also be passed through an analog to digital converter and stored on magnetic tape for processing in a computer.

It has been determined that by positioning the particle at about the focal plane of the lens 44, the ratio of the Fourier transform of the received pulse signal to the Fourier transform of the transmitted pulse signal is indicative of the density of the particle. With the acoustic wave focused, the signal reflected back from the focal plane is received with greatest intensity. Thus, even when the particle is part of a larger mass or is embedded in a less uniform mass than the gel, the ratio of the Fourier transforms of the signals is still a good indication of the density of the mass at the focal point of the lens. However, by making measurements in the uniform gel, a reference measurement which does not include any spurious signals can be obtained. Thereafter, when measurements are made in less ideal environments, the ratio of the Fourier transforms still closely follows the measurement obtained in the gel 22 for a particle of like density.

A primary use of the present system is in medical applications. Most ultrasonic imaging now used only detects an image of a reflecting object but does not indicate the characteristics of the material itself. The present system, that is a focusing lens used in conjunction with means for computing the Fourier transforms, can be used in conjunction with conventional scanners to characterize the object which is reflecting the incident wave. For example, one might use this system to characterize an unknown growth under the skin. To that end, the system shown in FIG. 1 would be used to generate characteristic reflections from different density tissues, including malignant tissue and the like. A table of known reflections can be established as a standard.

A conventional scanning device would then be used to locate the growth of concern. With the location of the growth identified, the proper focusing lens can be selected and positioned relative to the growth to focus an acoustic wave into the growth. Clear reflections are then obtained from the growth and the Fourier transform ratio can be computed. The ratio can be compared with the reference ratios to identify the unknown growth.

In order to provide for even clearer reflections, the received signal can be gated so that only reflections received from a distance which is equal to the focal distance of the lens are detected. Because the distance to the focal point is known, the time for the reflected wave to return from the growth particle to the lens at that distance can be calculated. An electronically timed detector gate can then be opened only at the time that the reflected wave is expected to allow only reflections from the area of interest to be detected.

Figure 2:
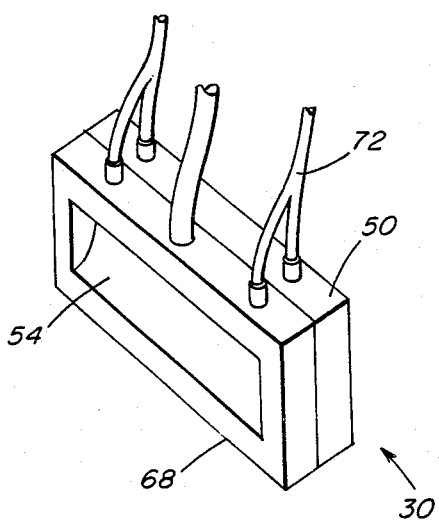
FIG. 2 is a perspective view of the transducer of FIG. 1.
Figure 3:
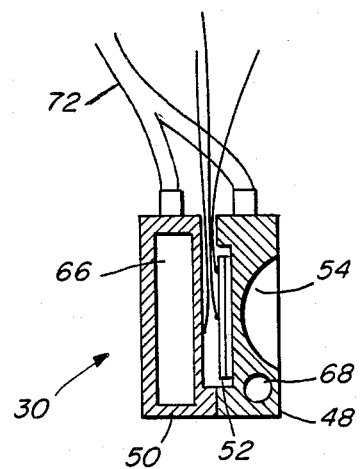
FIG. 3 is a cross sectional view of the transducer of FIGS. 1 and 2.
Figure 4:
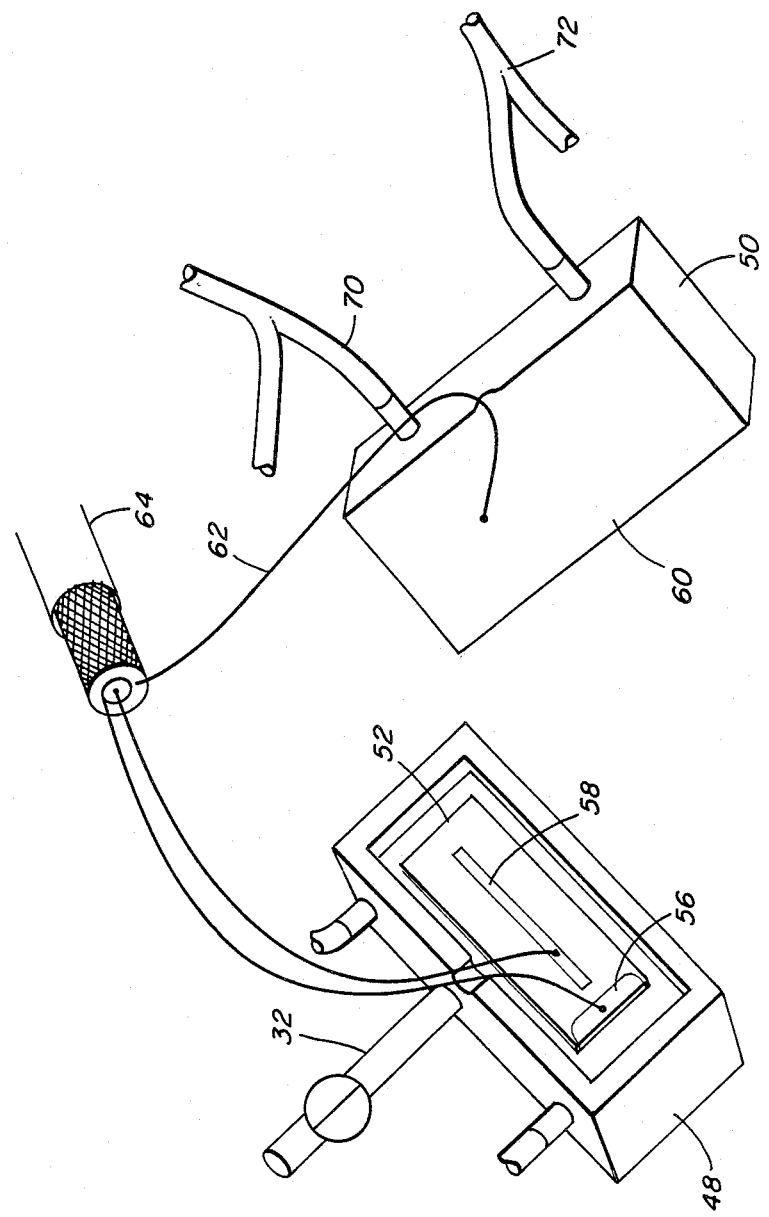
FIG. 4 is an exploded view of the two sections forming the transducer of FIGS. 1-3.

Details of the temperature controlled transducer assembly 30 are shown in FIGS. 2-4. The assembly includes two primary elements 48 and 50 between which a piezoelectric crystal 52 is sandwiched. A semi-cylindrical concavity 54 is formed in the front face of the section 48. Both sections are made of plexiglass. Thus acoustic waves which are transmitted from the crystal 52 through the section 48 and into the surrounding medium are focused onto a line by that lens surface. Alternatively, a semi-spherical concavity could be formed to focus the acoustic wave onto a point.

The crystal 52 is seated in a recess in the back surface of the section 48. The crystal is retained on the back surface of the section 48 by a conducting silver epoxy which adheres to a silver paint coating on the back surface of the section 48. As shown in FIG. 4, gold plated electrical contacts 56 and 58 are formed on the piezoelectric crystal. The inside surface 60 of the rear section 50 is coated with silver paint to shield the crystal and is connected through a lead 62 to the ground sleeve of the cable 64.

To provide for temperature control of the transducer assembly, a cavity 66 is formed throughout the rear section 50. Also, a U-shaped conduit 68 surrounds the lens concavity 54 in the front section. Both the cavity 66 and the conduit 68 are connected to inlet tubing 70 and outlet tubing 72 for circulating the warm or cold temperature control liquid.

The overall dimensions of the transducer assembly are 30 millimeters by 15 millimeters by 11 millimeters.

Figure 5:
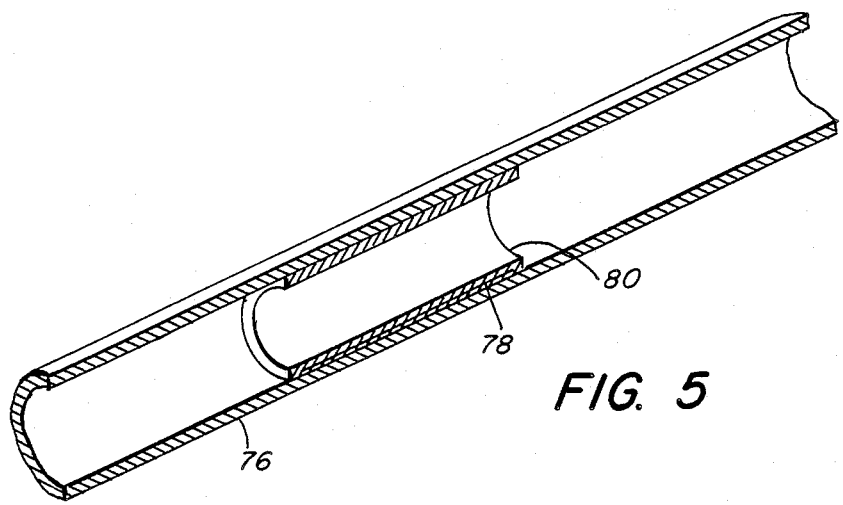
FIG. 5 is a broken away perspective view of an alternative embodiment of the invention for monitoring particles within a flow stream.

FIG. 5 illustrates an alternative transducer assembly for monitoring particles flowing in a tube 76. A piezoelectric crystal 78 is set in the back surface of a cylindrical plexiglass casing 80 which may be inserted in the tube 76. The casing 80 serves as a lens to focus the acoustic wave into the stream. Particles flowing through the casing can be characterized in the manner described above.

Figure 6:
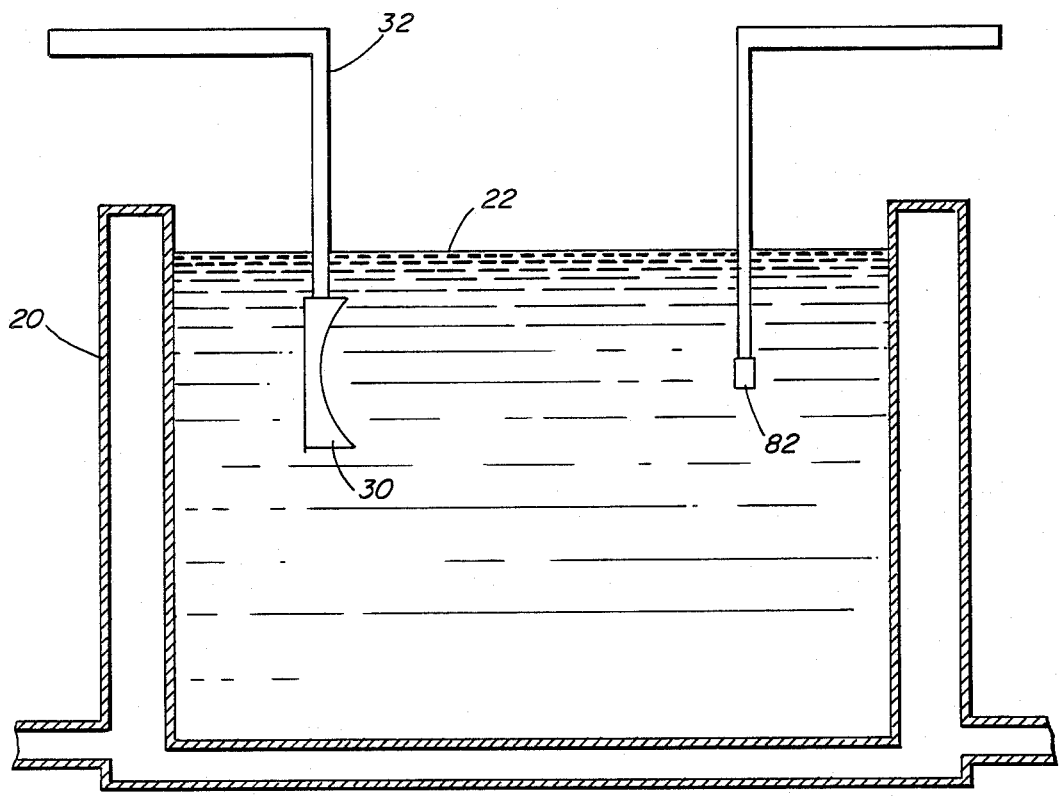
FIG. 6 is an illustration of an alternative use of the system of FIG. 1 in testing a lens with a hydrophone.

FIG. 6 illustrates an alternative use of the container 20 of FIG. 1. As before, a focusing transducer 30 is suspended in a gel 22. The purpose of the system of FIG. 6, however, is to measure the pressure field at various locations relative to the lens 30. To that end, a hydrophone probe 82 is positioned in the gel. By melting the gel surrounding either the transducer 30 or the hydrophone 82, the two can be moved relative to each other to make measurements at various relative positions and generate acoustic transmission curves relative to the transducer 30. In this system, either the transducer or the hydrophone can be temperature controlled or, because both elements can be suspended in the gel, the entire mass of gel may be melted to allow for movement of either the transducer or the hydrophone.

While the invention has been particularly shown and described with reference to preferred embodiments thereof, it will be understood by those skilled in the art that various changes in form and details may be made therein without departing from the spirit and scope of the invention as defined by the appended claims. The term acoustic refers to compression waves of ultrasonic as well as sonic frequencies.

I claim:

1. The method of ultrasonically monitoring a characteristic of a particle comprising:

suspending a particle in a low melting point medium;

applying a flow of heated liquid to an ultrasonic transducer to melt the low melting point medium only in the immediate area around said transducer;

moving said transducer to a second location within the low melting point medium;

applying a flow of relatively cool liquid to said transducer so as to solidify the area around said transducer;

transmitting an ultrasonic wave toward the particle by means of the ultrasonic transducer embedded in said low melting point medium; and monitoring ultrasonic waves reflected from the particle as an indication of said particle characteristics.

2. A method as claimed in claim 1 wherein an entire volume of the low melting point medium is melted and then resolidified to implant and suspend a particle within the medium.

3. A method as claimed in claim 2 wherein the acoustic wave is focused on the particle by the embedded transducer and the reflected wave from the particle is monitored by a receiving transducer which also focuses on the particle.

4. A method as claimed in claim 3 wherein a common acoustic transceiver serves as both transmitter and receiver.

5. A method of measuring an acoustic response comprising:

providing at least one acoustic transducer;

suspending at least the one acoustic transducer in a low melting point medium;

melting the low melting point medium surrounding the suspended transducer and relocating the suspended transducer within the medium;

cooling the low melting point medium surrounding the suspended transducer to resolidify the medium about the suspended transducer; and transmitting an acoustic wave relative to the suspended acoustic transducer through the low melting point medium and monitoring the acoustic waves in the medium such that the suspended transducer at least transmits or monitors the acoustic waves.

6. A method as claimed in claim 5 wherein the medium is melted by means of a temperature control liquid circulated through the transducer.

7. A method as claimed in claim 6 wherein the transducer is a focusing tranducer.

8. A method as claimed in claim 5 further comprising the steps of melting an entire volume of low melting point medium, resolidifying the medium while positioning a particle in the medium, subsequently heating a localized volume of medium about the transducer by means of a temperature control liquid directed through the transducer and moving the transducer into proper position relative to the particle, and focusing an acoustic wave from the transducer on the particle.

9. Apparatus for monitoring an acoustic transmission in a solid medium comprising:

a low melting point medium in a container;

an acoustic tranducer positioned within the medium;

means for melting the medium surrounding the transducer; and means for moving the transducer within the melted medium.

10. Apparatus as claimed in claim 9 further comprising means for circulating a temperature control liquid through the transducer.

11. Apparatus as claimed in claim 9 further comprising means for circulating a temperature control liquid for melting or solidifying the entire volume of medium.

12. Apparatus as claimed in claim 9 comprising a transmitting transducer for focusing a acoustic wave and a receiving transducer for detecting the acoustic wave, the receiving transducer being focused at a common point with the transmitting transducer.

13. Apparatus as claimed in claim 12 wherein the transmitter and receiver are a single transceiver element.

14. Apparatus as claimed in claim 12 further comprising an electronic processor for providing the ratio of the Fourier transform of the transmitted acoustic signal to the Fourier transform of the received acoustic signal.

15. Apparatus as claimed in claim 9 comprising a focusing acoustic transmitter and a hydrophone embedded in the medium.

16. Apparatus as claimed in claim 9 wherein the transducer comprises a first section having a lens concavity formed therein and a liquid conduit through the section around the lens and cavity, a back section with a liquid cavity therein, and a piezoelectric crystal between the front and rear sections.

* * * * *